US00PP23505P3

(12) United States Plant Patent
Bernabe

(10) Patent No.: US PP23,505 P3
(45) Date of Patent: Mar. 26, 2013

(54) *SALVIA* PLANT NAMED 'BLEU ARMOR'

(50) Latin Name: *Salvia hybrida*
Varietal Denomination: BLEU ARMOR

(76) Inventor: Catherine Bernabe, Henansal (FR)

( * ) Notice: Subject to any disclaimer, the term of this patent is extended or adjusted under 35 U.S.C. 154(b) by 0 days.

(21) Appl. No.: 13/199,124

(22) Filed: Aug. 19, 2011

(65) Prior Publication Data

US 2013/0047308 P1 Feb. 21, 2013

(51) Int. Cl.
*A01H 5/00* (2006.01)

(52) U.S. Cl. ..... Plt./475

(58) Field of Classification Search ..... Plt./475
See application file for complete search history.

*Primary Examiner* — Howard Locker

(57) ABSTRACT

A new and distinct *Salvia* cultivar named 'BLEU ARMOR' is disclosed, characterized by an attractive upright plant habit. 'BLEU ARMOR' produces blue flowers with a white eye continuously from May to November. The new variety is a *Salvia*, normally produced as an outdoor garden or container plant.

2 Drawing Sheets

Latin name of the genus and species: *Salvia hybrida*.
Variety denomination: 'BLEU ARMOR'.

BACKGROUND OF THE INVENTION

The new cultivar is a product of a planned breeding program conducted by the inventor, Catherine Bernabe, a citizen of France. The objective of the breeding program was to produce *Salvia* plants with attractive plant shapes in a variety of colors. Various unnamed, unpatented *Salvia* plants were either self-crossed, or open pollinated during the Summer of 2008, at a commercial nursery in Henansal, France. The new variety was discovered as a single plant in the Spring of 2009, at the same commercial nursery by the inventor, Catherine Bernabe, in a group of seedlings resulting from the open pollination.

Asexual reproduction of the new cultivar 'BLEU ARMOR' by vegetative cuttings was first performed at the same commercial greenhouse in Henansal, France in 2009 and has shown that the unique features of this cultivar are stable and reproduced true to type on successive generations.

SUMMARY OF THE INVENTION

The cultivar 'BLEU ARMOR' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BLEU ARMOR' These characteristics in combination distinguish 'BLEU ARMOR' as a new and distinct *Salvia* cultivar:

1. Dark blue flower with a white spot.
2. Well shaped, bushy plant habit.
3. Continuous flowering from May to November.
4. Upright plant habit.

COMMERCIAL COMPARISONS

Plants of the new cultivar 'BLEU ARMOR' can be compared to the unpatented *Salvia lycoides*. Plants of 'BLEU ARMOR' are similar to plants of, *Salvia lycoides* in most horticultural characteristics, however, plants of the new cultivar 'BLEU ARMOR' are overall larger, and produce larger foliage. 'BLEU ARMOR' also produces flowers that are more true blue, less violet colored than *Salvia lycoides*.

Plants of the new cultivar 'BLEU ARMOR' can also be compared to the unpatented *Salvia chamaedryoides*. Plants of 'BLEU ARMOR' are similar to plants of, *Salvia chamaedryoides* in most horticultural characteristics, however, plants of the new cultivar 'BLEU ARMOR' are more vigorous, with a more round, upright and attractive plant habit. 'BLEU ARMOR' also produces green foliage, compared to the blue-grey foliage of *Salvia chamaedryoides*.

Plants of the new cultivar 'BLEU ARMOR' can also be compared to the unpatented variety *Salvia hybrida* 'Nuit d'Armor'. Plants of 'BLEU ARMOR' are similar to plants of, *Salvia hybrida* 'Nuit d'Armor' in most horticultural characteristics, however, plants of the new cultivar 'BLEU ARMOR' are more upright, and less spreading than plants of 'Nuit d'Armor'

BRIEF DESCRIPTION OF THE PHOTOGRAPHS

Figure 1:
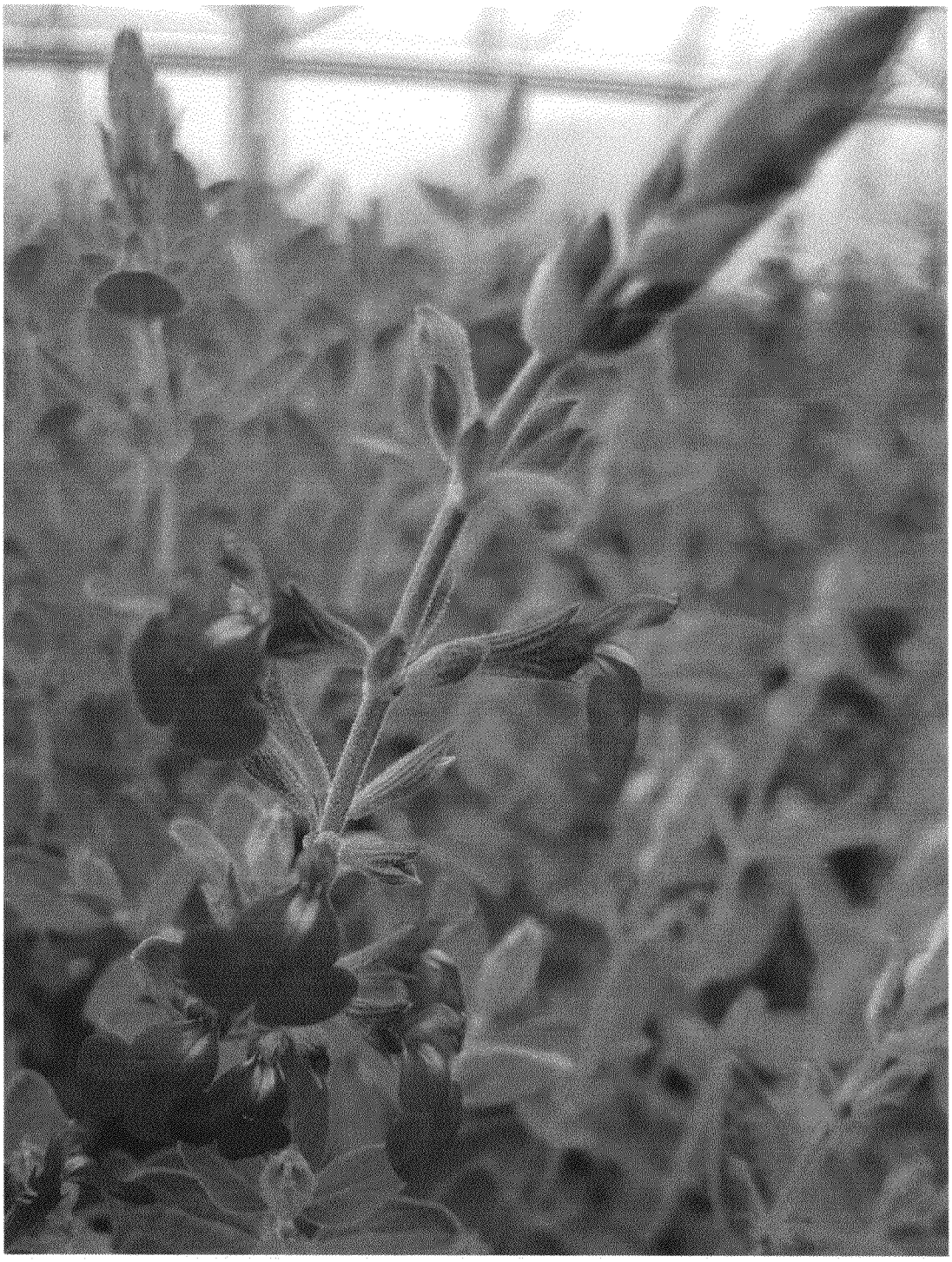

The accompanying photograph in FIG. 1 illustrates in full color a flower spike from a plant of 'BLEU ARMOR'.

Figure 2:
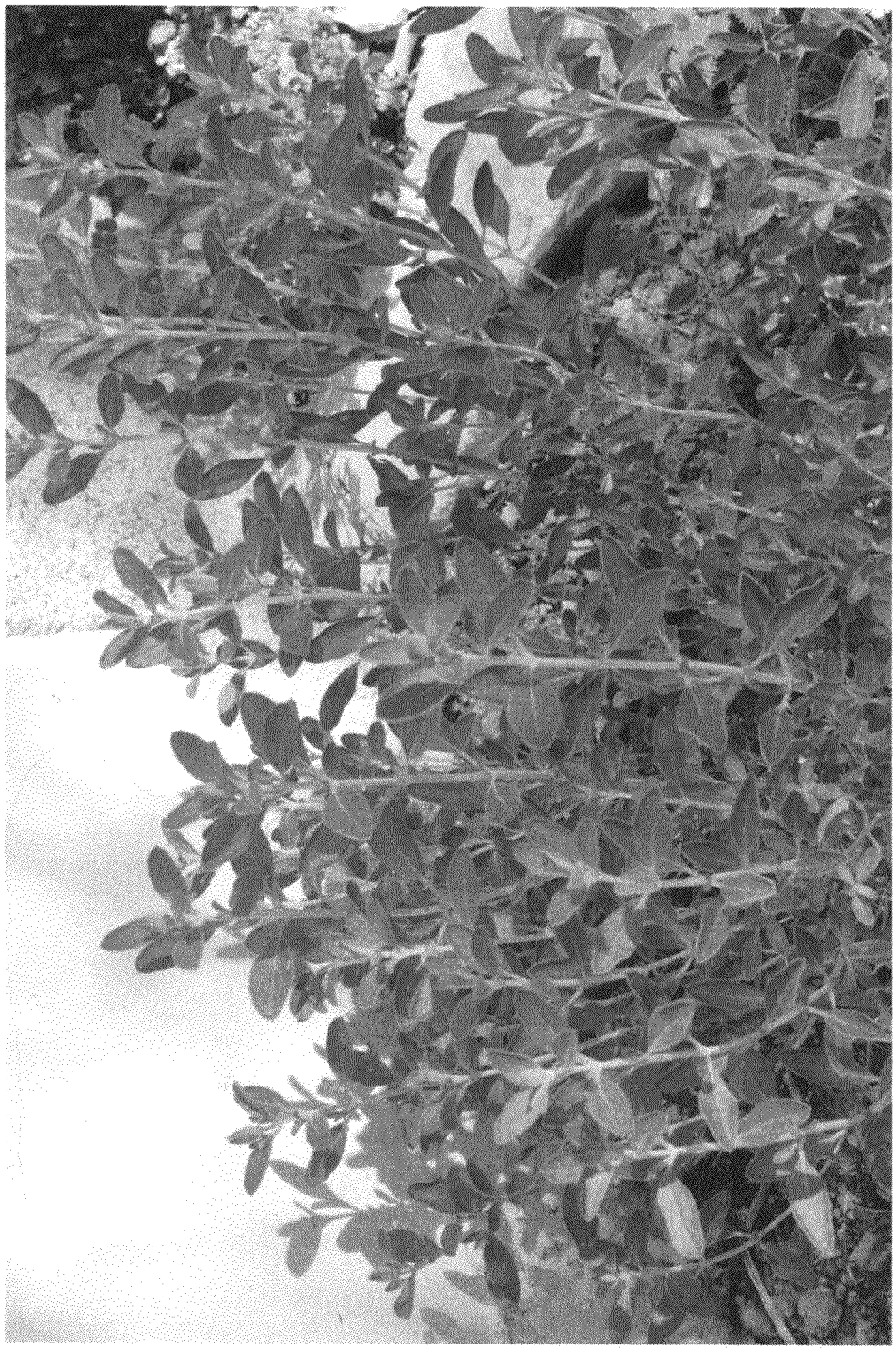

FIG. 2 illustrates in full color typical plant of 'BLEU ARMOR' grown outdoors, in a garden. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'BLEU ARMOR' plants grown outdoors at a commercial nursery in Henansal, France. The growing temperature ranged from 8° C. to 28° C., day and night. The nursery area is un-shaded, giving bright, normal sunlight conditions. Measurements and numerical values represent averages of typical plant types.

Botanical classification: *Salvia hybrida* 'BLEU ARMOR'.

PROPAGATION

Time to initiate roots: About 10 days at approximately 20° C.

Time to produce a rooted cutting: About 20 to 25 days at 20° C.

PLANT

Plant spread: Approximately 60 to 70 cm.

Plant height: Approximately 60 cm.

Growth rate: Moderate

Length of primary lateral branches: Approximately 30 to 35 cm.

Diameter of lateral branches: Approximately 0.20 to 0.30 cm.

Quantity of lateral branches: About 50 to 60.

Stem:

- *Color*.—Young: Near RHS Green-Yellow 145A and oldest: Near RHS Greyed-Orange 165A.
- *Texture/pubescence*.—Smooth.

Internode length: Approximately 3.5 to 4.5 cm.

Age of plant described: Approximately 30 weeks in a 2 liter container.

FOLIAGE

Leaf:

- *Arrangement*.—Opposite.
- *Quantity*.—Approximately 10 to 12 per main branch.
- *Average length*.—Approximately 3.5 to 5.5 cm.
- *Average width*.—Approximately 1.0 to 1.6 cm.
- *Shape of blade*.—Young: linear. Mature: elliptic.
- *Apex*.—Acute.
- *Base*.—Attenuate.
- *Attachment*.—Stalked.
- *Margin*.—Lightly crenate with small cilium.
- *Texture of top surface*.—Non pubescent.
- *Texture of bottom surface*.—Non pubescent.
- *Foliage scent*.—Weak aroma, typical of *Salvia* when crushed.
- *Color*.—Young foliage upper side: Near RHS Yellow green 137C. Young foliage under side: Near RHS Yellow green 138B. Mature foliage upper side: Near RHS green 137A. Mature foliage under side: Near RHS green 138A.
- *Venation*.—Type: Pinnate. Venation color upper side: Near RHS yellow green 145A. Venation color under side: Near RHS yellow green 138B on base of leaf and 145A on the upper section.
- *Petiole*.—Average Length: Approximately 0.8 to 1.2 cm. Diameter: Approximately 0.1 cm. Color: Near RHS yellow green 145A.

FLOWER

Natural flowering season: May to November.

Inflorescence type and habit: Flowers arranged in verticillasters on spikes.

Flower longevity on plant: 8 days.

Quantity of flowers: About 15 to 20 buds and 8 to 10 fully opened flowers per lateral branch, at one time; or about 50 to 60 blooming spikes per plant.

Inflorescence size:

- *Diameter/width*.—Approximately 3 to 4 cm.
- *Height*.—Approximately 17 to 18 cm.

Individual flower size:

- *Length*.—Approximately 2.5 cm.
- *Width*.—Approximately 1.2 cm.

Peduncle:

- *Length*.—0.4 to 0.50 cm.
- *Diameter*.—0.10 cm.
- *Color*.—Near RHS Yellow-Green 145A.
- *Orientation*.—Nearly completely vertical (10 degrees angle).
- *Strength*.—Rigid.

Petals:

- *Petal arrangement*.—Fused: flower-cup with 2 lips.
- *Margin*.—Entire.
- *Length*.—Lower lip: 1.1 to 1.2 cm upper lip: 1.8 to 2.0 cm.
- *Width*.—Lower lip: 1.1 to 1.4 cm upper lip: 0.2 to 0.4 cm.
- *Petal quantity*.—2 lips.
- *Petal apex shape*.—Lobate for lower lip.
- *Texture*.—Smooth to somewhat velvety.
- *Color*.—Petals: When opening: Upper surface: Near RHS Violet-Blue 95A. Lower surface: Near RHS Violet-Blue 96C. Fully opened: Upper surface: Near RHS Violet-Blue 95B with interior spot White N155D. Lower surface: Near RHS Violet-Blue N88A and White N155D.

Bud:

- *Shape*.—Elongated cylinder.
- *Length*.—0.8 to 1.0 cm.
- *Diameter*.—0.2 to 0.3 cm.
- *Color*.—Near RHS Violet-Blue 95A.

Sepals:

- *Shape*.—Fused cylinder.
- *Quantity per flower*.—3, one large sepal, and two somewhat smaller.
- *Length*.—Approximately 1.0 to 1.2 cm.
- *Width*.—Approximately largest 0.3 cm and 2 smaller: 0.2 cm.
- *Apex*.—Acute.
- *Margin*.—Entire.
- *Texture*.—Pubescent.
- *Color*.—Near RHS Yellow-Green 145A on base. Upper length of sepal Yellow-Green 147A and Greyed-Purple N186A.

REPRODUCTIVE ORGANS

Stamens:

- *Number*.—2.
- *Filament length*.—Approximately 0.8 to 0.9 cm.

Anthers:

- *Shape*.—Linear.
- *Length*.—Approximately 0.15 cm. Color: Near RHS White N155D.
- *Pollen*.—Color: Near RHS Yellow orange 17A to B. Quantity: Moderate.

Pistil:

- *Number*.—1.
- *Length*.—Approximately 1.8 to 1.9 cm.
- *Style*.—Length: Approximately 1.6 to 1.7 cm. Color: Near RHS White NN155D.

*Stigma*.—Shape: linear. Color: Near RHS Violet-Blue N89A. Ovary color: Near RHS Yellow 10B.

OTHER CHARACTERISTICS

Seeds and fruits: Irregular sphere-shaped nutlets, 4 per flower typically. Colored near Grey-Brown 199A.

Disease/pest resistance: Neither resistance nor susceptibility to pathogens and pests common to *Salvia* have been observed.

Temperature tolerance: The new variety tolerates temperatures approximately between 10° C. and 40° C.

What is claimed is:

1. A new and distinct cultivar of *Salvia* plant named 'BLEU ARMOR' as herein illustrated and described.

* * * * *